US010085932B2

(12) United States Patent
Alves et al.

(10) Patent No.: US 10,085,932 B2
(45) Date of Patent: Oct. 2, 2018

(54) COSMETIC COMPOSITION COMPRISING LIQUID FATTY ESTERS, VOLATILE OILS AND THICKENERS, AND COSMETIC TREATMENT PROCESSES

(71) Applicant: L'OREAL, Paris (FR)

(72) Inventors: Diego Alves, Rio de Janeiro (BR); Leandro Carvalho, Rio de Janeiro (BR); Megumi Nishitani Yukuyama, Rio de Janeiro (BR); Divye Mykaela Carbonera, Copacabana (BR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/906,068

(22) PCT Filed: Jul. 4, 2014

(86) PCT No.: PCT/EP2014/064284
§ 371 (c)(1),
(2) Date: Jan. 19, 2016

(87) PCT Pub. No.: WO2015/001069
PCT Pub. Date: Jan. 8, 2015

(65) Prior Publication Data
US 2016/0151272 A1 Jun. 2, 2016

(30) Foreign Application Priority Data

Jul. 4, 2013 (FR) ..................................... 13 56564

(51) Int. Cl.
*A61K 8/90* (2006.01)
*A61K 8/25* (2006.01)
*A61K 8/29* (2006.01)
*A61K 8/31* (2006.01)
*A61K 8/37* (2006.01)
*A61Q 5/06* (2006.01)
*A61Q 5/12* (2006.01)
*A61K 8/02* (2006.01)
*A61K 8/04* (2006.01)
*A61K 8/19* (2006.01)
*A61K 8/26* (2006.01)

(52) U.S. Cl.
CPC .............. *A61K 8/90* (2013.01); *A61K 8/0241* (2013.01); *A61K 8/042* (2013.01); *A61K 8/19* (2013.01); *A61K 8/25* (2013.01); *A61K 8/26* (2013.01); *A61K 8/29* (2013.01); *A61K 8/31* (2013.01); *A61K 8/37* (2013.01); *A61K 8/375* (2013.01); *A61Q 5/06* (2013.01); *A61Q 5/065* (2013.01); *A61Q 5/12* (2013.01); *A61K 2800/31* (2013.01); *A61K 2800/43* (2013.01); *A61K 2800/48* (2013.01); *A61K 2800/596* (2013.01); *A61K 2800/651* (2013.01)

(58) Field of Classification Search
CPC ........ A01N 25/04; A01N 25/18; A01N 53/00; A01N 2300/00; A01N 37/18; A01N 49/00; A01N 25/006; A61Q 19/00; A61Q 15/00; A61Q 17/04; A61Q 1/02; A61Q 5/10; A61Q 19/04; A61Q 1/10; A61Q 5/065; A61Q 5/08; A61Q 5/12; A61Q 13/00; A61Q 19/08; A61Q 1/00; A61Q 1/14; A61Q 5/00; A61K 8/31; A61K 8/37; A61K 8/891; A61K 2800/43; A61K 8/042; A61K 8/90; A61K 2800/31; A61K 2800/412; A61K 2800/4322; A61K 2800/624; A61K 2800/88; A61K 31/635; A61K 47/183; A61K 8/0241; A61K 8/06; A61K 8/062; A61K 8/11; A61K 8/33; A61K 8/8117; A61K 9/0048; A61K 9/1647; A61K 2300/00; A61K 31/00; A61K 31/505; A61K 47/06; A61K 47/32; A61K 8/492; A61K 8/671; A61K 8/85; A61K 9/0014; A61K 9/5146; A61K 9/5153; A61K 9/5161; A61K 2800/413
See application file for complete search history.

(56) References Cited

U.S. PATENT DOCUMENTS 4,578,266 A    3/1986  Tietjen et al.
5,221,534 A *  6/1993  DesLauriers .......... A61K 8/042
                                             424/401
(Continued)

FOREIGN PATENT DOCUMENTS

EP    1029587 A    8/2000
EP    1184426 A2   3/2002
(Continued)

OTHER PUBLICATIONS

International Search Report for PCT/EP2014/064284 (dated Nov. 6, 2014).
Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
Bouchemal, K., "Microencapsulation of Dehydroepiandrosterone (DHEA) with Poly(Ortho Ester) Polymers by Interfacial Polycondensation," Journal of Microencapsulation, 2003, vol. 20, No. 5, pp. 637-651.
Bezemer, J.M., "Microspheres for Protein Delivery Prepared from Amphiphilic Multiblock Copolymers," Journal of Controlled Release, 67, 2000, pp. 233-248.
International Search Report and Written Opinion cited in counterpart PCT Application No. PCT/EP2014/064284, dated Nov. 6, 2014.

*Primary Examiner* — Audrea B Coniglio
(74) *Attorney, Agent, or Firm* — The Marbury Law Group, PLLC

(57) ABSTRACT

The present invention relates to a cosmetic composition which is preferentially anhydrous, comprising from 10% to 40% by weight of liquid fatty esters, at least 30% by weight of volatile oils other than the liquid fatty esters, and thickeners. The composition may also comprise particles that are insoluble in the medium, such as pigments or microcapsules. The invention also relates to a cosmetic treatment process, especially for caring for or conditioning the hair, using this composition, which is more particularly intended for curly or frizzy hair.

19 Claims, No Drawings

(56) References Cited

U.S. PATENT DOCUMENTS

| | | |
|---|---|---|
| 5,645,609 A | 7/1997 | Andrean et al. |
| 5,871,765 A | 2/1999 | Johnson et al. |
| 5,980,948 A | 11/1999 | Goedemoed et al. |
| 6,565,886 B1 | 5/2003 | Simonnet et al. |
| 2002/0055562 A1* | 5/2002 | Butuc .................. A61K 8/042 524/80 |
| 2003/0224060 A1 | 12/2003 | Simonnet et al. |
| 2007/0179204 A1 | 8/2007 | Butuc et al. |
| 2012/0003172 A1* | 1/2012 | Desenne ................ A61K 8/31 424/70.9 |
| 2013/0019414 A1* | 1/2013 | Hercouet ............... A61K 8/31 8/406 |

FOREIGN PATENT DOCUMENTS

| | | | |
|---|---|---|---|
| EP | 1342471 A1 | 9/2003 | |
| EP | 2345401 A1 * | 7/2011 | ............. A61K 8/31 |
| EP | 2345401 A1 | 7/2011 | |
| FR | 2679771 A1 | 2/1993 | |
| FR | 2921261 A1 | 3/2009 | |
| WO | 2009/037347 A2 | 3/2009 | |

\* cited by examiner

COSMETIC COMPOSITION COMPRISING LIQUID FATTY ESTERS, VOLATILE OILS AND THICKENERS, AND COSMETIC TREATMENT PROCESSES

CROSS REFERENCE TO RELATED APPLICATIONS

This is a national stage application of PCT/EP2014/064284, filed internationally on Jul. 4, 2014, which claims priority to French Application No. 1356564, which was filed on Jul. 4, 2013, both of which are incorporated by reference herein in their entireties.

The present invention relates to cosmetic compositions, especially hair compositions, comprising a combination of a volatile oil, a fatty ester and a thickener.

Many people are dissatisfied with the appearance of their hair; in particular, people who have curly hair usually wish to obtain straight hair, and, conversely, people who have curl-free hair wish to have curly hair.

Various techniques are known that are usually used for obtaining wavy or straight hair, either permanently, for example using a chemical treatment, or temporarily, for example by hairsetting.

However, these techniques may result in impairment of the hair fibres in the case of chemical treatments with reducing and oxidizing agents, or with alkaline hydroxides, or else may provide shaping that is not particularly natural, as in the case of using film-forming polymers, for example.

Oily sera and hair oils for improving the straightness of the hair from a visual point of view, especially by reducing the frizziness, while at the same time imparting manageability and a certain level of control of the volume of the head of hair, have also been proposed. However, the performance of these products is still not optimal, especially from the point of view of the efficacy in reducing the frizziness, the ease of application of the composition, the ability to convey other active materials and the final cosmeticity of the treated hair.

Consumers are therefore still in search of optimized compositions, for obtaining adequate visual straightness of the hair and control, or even elimination, of frizziness, and also control or reduction of the volume and of the apparent mass of the head of hair, the said compositions thus being most particularly suitable for curly and/or voluminous hair.

The aim of the present invention is to overcome the drawbacks of the prior art and to propose cosmetic compositions that are easy to apply to the hair and that are capable of giving both (i) straightness to the head of hair, from a visual point of view, the said straightness being reflected by a disappearance of the frizziness, and (ii) control of the volume of the head of hair, or even a reduction of its apparent volume, giving the hair a very satisfactory final cosmetic state.

Thus, one subject of the present invention is a cosmetic composition comprising:
 (a) one or more liquid fatty esters in an amount ranging from 10% to 40% by weight relative to the total weight of the composition,
 (b) one or more volatile oils, other than the liquid fatty esters (a), in an amount of greater than or equal to 30% by weight relative to the total weight of the composition,
 (c) one or more thickeners, and
 (d) one or more insoluble particles.

Another subject of the invention is a cosmetic treatment process, especially for caring for, cleansing and/or conditioning keratin materials, especially the hair, comprising the application to the said materials of a cosmetic composition as defined above, optionally followed by rinsing, for example with water, after an optional leave-in time.

Another subject of the invention is a cosmetic process for treating the hair, especially for caring for, cleansing and/or conditioning the hair, comprising the application of a cosmetic composition comprising:
 (a) one or more liquid fatty esters in an amount ranging from 10% to 40% by weight relative to the total weight of the composition,
 (b) one or more volatile oils, other than the liquid fatty esters (a), in an amount of greater than or equal to 30% by weight relative to the total weight of the composition, and
 (c) one or more thickeners chosen from optionally hydrogenated block, especially diblock or triblock, copolymers of styrene and of olefin, preferably containing one or two ethylenic unsaturations, and/or preferably containing from 2 to 5 carbon atoms,
optionally followed by rinsing, for example with water, after an optional leave-in time.

In the said hair treatment process, the composition may also comprise one or more insoluble particles, especially as defined below, and in particular chosen from pigments, especially nacres and microcapsules.

The compositions can also give the hair manageability, the hair then readily resuming the shape that it has been given during styling; and also a soft feel and sheen.

In addition, it has been observed that the compositions according to the invention have an adequate viscosity, which may go as far as producing a gelled texture, which may allow easy application, and also the suspension within the composition of encapsulated agents and/or of particles such as micas, thus allowing a wide variety of visual effects.

Advantageously, the composition obtained has a malleable and better still transparent gelled texture. The composition is also very light, even if it contains oils.

The composition according to the invention preferably has a texture that is halfway between that of a styling gel and that of a hair oil; this texture is likened to that of a thickened or even gelled oil, which allows the incorporation of insoluble particles, and leads to cosmetic properties especially after it has been applied to the hair, such as a softer feel.

This composition may also make it possible to control frizziness and to treat damaged ends.

In the present description, the term "at least one" is equivalent to the expression "one or more", and the term "between . . . and . . . " is equivalent to the term "ranging from . . . to . . . ", which implies that the limits are included.

Liquid Fatty Ester

The composition according to the invention thus comprises one or more liquid fatty esters.

The term "liquid fatty ester" means an ester that is liquid at room temperature and atmospheric pressure (25° C., 1 atm) and which comprises in its structure at least one hydrocarbon-based chain containing at least 6 carbon atoms. Preferably, it has a melting point of less than or equal to 10° C.

The liquid fatty esters may be esters of monoalcohols or of polyols with monocarboxylic or polycarboxylic acids, at least one of the alcohols and/or acids comprising at least one hydrocarbon-based chain containing at least 6 carbon atoms. These liquid fatty esters may be glycerol esters and especially natural or synthetic mono-, di- or triglycerides, such as plant oils (non-volatile), for instance sunflower oil, corn oil, soybean oil, marrow oil, grapeseed oil, pracaxi oil, argan oil, sesame oil, hazelnut oil, apricot oil, macadamia oil, arara oil, castor oil, avocado oil, jojoba oil or shea butter oil.

Preferably, the liquid fatty ester according to the invention is chosen from esters of a fatty acid (at least 6 carbon atoms) and of a monoalcohol, more particularly from esters of a fatty monoacid and of a monoalcohol. Preferably, at least one of the alcohols and/or acids is branched. Preferably, the alcohol and/or the acid are saturated, and preferentially both are saturated. Preferentially, the liquid fatty ester is not oxyalkylenated.

The liquid fatty esters according to the invention are preferably of formula R1-COOR2, in which:

R1 denotes a linear or branched, saturated or unsaturated, optionally mono- or polyhydroxylated hydrocarbon-based radical, containing from 5 to 31 carbon atoms, preferably containing from 7 to 21 carbon atoms, and R2 denotes a linear or branched, saturated or unsaturated, optionally mono- or polyhydroxylated hydrocarbon-based radical, containing from 1 to 20 carbon atoms.

Preferably, R1 denotes a linear or branched alkyl (saturated) radical containing 7 to 21 carbon atoms, especially from 8 to 17 carbon atoms, and more preferably from 8 to 15 carbon atoms.

Preferably, R2 denotes a linear alkyl (saturated) radical containing 1 to 4 carbon atoms or a branched alkyl (saturated) radical containing from 3 to 20 carbon atoms, especially from 3 to 16 carbon atoms. More preferably, R2 denotes a branched saturated alkyl radical containing from 3 to 12 carbon atoms.

Mention may be made of ethyl laurate, butyl laurate, hexyl laurate, isohexyl laurate, isopropyl laurate, methyl myristate, ethyl myristate, butyl myristate, isobutyl myristate, isopropyl myristate, 2-octyldodecyl myristate, 2-ethylhexyl monococoate (or octyl monococoate), ethyl palmitate, isopropyl palmitate, isobutyl palmitate, 2-ethylhexyl palmitate (or octyl palmitate), butyl stearate, isopropyl stearate, isobutyl stearate, isocetyl stearate, isostearyl isostearate, isopropyl isostearate, 2-ethylhexyl stearate (or octyl stearate), 2-ethylhexyl hydroxystearate (or octyl hydroxystearate), decyl oleate, isononyl isononanoate, tridecyl neopentanoate, isocetyl neopentanoate, isostearyl neopentanoate, octyldodecyl neopentanoate and isoarachidyl neopentanoate, and mixtures thereof.

Preferably, the liquid fatty ester used in the invention is chosen from isopropyl myristate, methyl myristate, ethyl myristate, butyl myristate, isobutyl myristate, 2-octyldodecyl myristate, 2-ethylhexyl monococoate (or octyl monococoate), ethyl palmitate, isopropyl palmitate, isobutyl palmitate, 2-ethylhexyl palmitate (or octyl palmitate), butyl stearate, isopropyl stearate, isobutyl stearate, isocetyl stearate, isostearyl isostearate, isopropyl isostearate, 2-ethylhexyl stearate (or octyl stearate), isononyl isononanoate, 2-ethylhexyl hydroxystearate (or octyl hydroxystearate) and decyl oleate, and mixtures thereof; and more particularly from isopropyl myristate, isononyl isononanoate and isopropyl palmitate, and mixtures thereof.

The compositions according to the invention comprise the said liquid fatty ester(s) in an amount ranging from 10% to 40% by weight, preferably from 10% to 35% by weight, preferentially from 12% to 30% by weight and better still from 12% to 25% by weight, relative to the total weight of the composition.

Volatile Oil

The composition according to the invention also comprises one or more volatile oils, other than the liquid fatty esters above.

Preferably, the volatile oil is non-silicone, i.e. it does not comprise in its structure a sequence of several siloxane units Si—O.

For the purposes of the present invention, the term "volatile oil" means an oil that is capable of evaporating on contact with a keratin surface at room temperature (20° C.) and at atmospheric pressure (1 atm), preferably in less than one hour. At room temperature and atmospheric pressure it is liquid and especially has a non-zero vapour pressure, in particular ranging from 0.13 Pa to 40 000 Pa ($10^{-3}$ to 300 mmHg), especially ranging from 1.3 Pa to 13 000 Pa (0.01 to 100 mmHg) and more particularly ranging from 1.3 Pa to 1300 Pa (0.01 to 10 mmHg).

The volatile oil(s) are advantageously chosen from hydrocarbon-based oils comprising 8 to 16 carbon atoms, and especially branched C8-C16 alkanes (also known as isoparaffins), for instance isododecane, isodecane or isohexadecane; linear C8-C16 and especially C11-C15 alkanes, such as undecane and tridecane; mention may be made especially of the oils sold under the trade names Isopar or Permethyl.

The compositions according to the invention comprise the said volatile oil(s) in an amount of greater than or equal to 30% by weight relative to the total weight of the composition, and especially in an amount ranging from 30% to 98% by weight, preferably from 35% to 97% by weight, preferentially from 40% to 95% by weight and better still from 45% to 95% by weight, relative to the total weight of the composition.

Thickener

The composition according to the invention also comprises one or more thickeners.

For the purposes of the present invention, the term "thickener" means a compound that is capable, by virtue of its presence, at 25° C., of increasing the viscosity of the composition in which it is present, preferably by at least 50 cps (centipoises).

The thickeners may be chosen from non-polymeric thickeners and polymeric thickeners or thickening polymers.

The thickening polymer that is preferred is a polymer having, as a solution or dispersion containing 1% by weight of active material in water, in ethanol, in liquid paraffin, in isopropyl myristate or in D5 cyclic silicone, at 25° C., a viscosity greater than 0.2 poise at a shear rate of 1 $s^{-1}$. The viscosity is measured with a Haake RS600 viscometer from Thermo Electron, which is an imposed-stress viscometer with cone-plate geometry (for example 60 mm in diameter).

Preferably, the thickener is a thickening polymer, preferentially a non-silicone thickening polymer, and may be chosen from associative or non-associative acrylic thickening polymers; modified or unmodified, associative or non-associative polymers bearing sugar units; block polymers.

Advantageously, the thickener that may be used in the context of the present invention is chosen from block, especially diblock or triblock, or even multiblock, radial or star polymers, and a mixture thereof; the polymer preferably being diblock or triblock.

Such polymeric thickeners are described especially in patent application US-A-2002/005 562 and in U.S. Pat. No. 5,221,534.

Advantageously, the thickener is an amorphous block, especially diblock or triblock, copolymer of styrene and of olefin(s).

Examples of olefins that may be mentioned include ethylenic carbide monomers especially containing one or two ethylenic unsaturations, containing from 2 to 5 carbon atoms, such as ethylene, propylene, butylene, butadiene and isoprene.

The polymeric thickener of block polymer type is preferably hydrogenated to reduce the residual ethylenic unsaturations after polymerization of the monomers.

In particular, the said thickener is an optionally hydrogenated copolymer, bearing styrene blocks and ethylene and/or C3-C5 and especially C3-C4 alkylene blocks, and especially butylene or propylene.

It may be a diblock copolymer, which is preferably hydrogenated, bearing styrene blocks and ethylene/C3-C4 alkylene blocks, more particularly a diblock copolymer, which is preferably hydrogenated, bearing styrene blocks and ethylene/propylene or ethylene/butylene blocks. Mention may also be made of diblock copolymers, which are preferably hydrogenated, bearing styrene and ethylene/butadiene blocks. Such diblock polymers are especially commercially available under the name Kraton® G1701E by the company Kraton Polymers.

It may also be a triblock copolymer, which is preferably hydrogenated, chosen from styrene-ethylene/propylene-styrene copolymers, styrene-ethylene/butadiene-styrene copolymers, styrene-isoprene-styrene copolymers and styrene-butadiene-styrene copolymers. Such triblock polymers are especially commercially available under the names Kraton® G1650, Kraton® G1652, Kraton® D1101, Kraton® D1102 and Kraton® D1160 by the company Kraton Polymers.

A mixture of hydrogenated styrene-butylene/ethylene-styrene triblock copolymer and of ethylene-propylene-styrene hydrogenated star polymer may also be used, such a mixture especially being in isododecane. Such mixtures are sold, for example, by the company Penreco under the trade names Versagel® M5960 and Versagel® M5670.

Preferably, the thickeners are chosen from diblock copolymers, which are preferably hydrogenated, bearing styrene blocks and ethylene/C3-C4 alkylene blocks, more particularly copolymers, which are preferably hydrogenated, bearing styrene blocks and ethylene/propylene or ethylene/butylene blocks.

The composition according to the invention comprises the thickener(s) in an amount preferably ranging from 0.1% to 20% by weight, especially from 0.1% to 15% by weight, better still from 0.1% to 10% by weight, in particular from 0.5% to 8% by weight, or even from 1% to 6% by weight, relative to the total weight of the composition.

Insoluble Particles

In one preferred embodiment, the compositions according to the invention may also comprise one or more insoluble particles.

Specifically, it has been observed that the compositions according to the invention enable, by virtue of their gelled texture, the suspension of insoluble particles in the medium; these particles may thus be present in large amounts in the composition, while at the same time conserving a homogeneous suspension (no destabilization of the composition, for example no settling-out of the said particles).

It is thus possible to obtain a wide diversity of visual effects for the composition.

The said insoluble particles are, of course, different from the above thickeners. The term "insoluble particles" means particles which do not form a single macroscopic phase in the medium comprising them, at 25° C., 1 atm, at a concentration of 1% by weight. In the context of the present invention, the said medium consists mainly of the liquid fatty esters and the volatile oils, and also the thickeners. Advantageously, the said particles are chosen from pigments and especially nacres, and microcapsules, and also a mixture thereof.

In a particular embodiment of the invention, the cosmetic composition may thus comprise at least one pigment.

The term "pigment" means any pigment that gives colour to compositions and/or to keratin materials. Their solubility in water at 25° C. and at atmospheric pressure (760 mmHg) is less than 0.05% and preferably less than 0.01% by weight.

The pigments that may be used may be chosen from organic and/or mineral pigments known in the art, especially those described in the Kirk-Othmer *Encyclopedia of Chemical Technology* and in Ullmann's *Encyclopedia of Industrial Chemistry*.

These pigments may be in the form of powder or of pigmentary paste. They can be coated or uncoated.

The pigments may be chosen, for example, from mineral pigments, organic pigments, lakes, pigments with special effects, such as nacres or glitter flakes, and mixtures thereof.

The term "mineral pigment" means any pigment that satisfies the definition in Ullmann's encyclopaedia in the chapter on inorganic pigments. Mention may be made especially of iron oxides, chromium oxides, manganese violet, ultramarine blue, chromium hydrate, ferric blue and titanium oxide.

The term "organic pigment" means any pigment that satisfies the definition in Ullmann's encyclopaedia in the chapter on organic pigments. The organic pigment may especially be chosen from nitroso, nitro, azo, xanthene, quinoline, anthraquinone, phthalocyanin, metal complex, isoindolinone, isoindoline, quinacridone, perinone, perylene, diketopyrrolopyrrole, thioindigo, dioxazine, triphenylmethane and quinophthalone compounds. In particular, the white or coloured organic pigments may be chosen from carmine, carbon black, aniline black, azo yellow, quinacridone, phthalocyanin blue, sorghum red, the blue pigments codified in the Color Index under the references CI 42090, 69800, 69825, 73000, 74100, 74160, the yellow pigments codified in the Color Index under the references CI 11680, 11710, 15985, 19140, 20040, 21100, 21108, 47000, 47005, the green pigments codified in the Color Index under the references CI 61565, 61570, 74260, the orange pigments codified in the Color Index under the references CI 11725, 15510, 45370, 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, 75470, the pigments obtained by oxidative polymerization of indole or phenolic derivatives as described in patent FR 2 679 771.

The pigments may also be in the form of composite pigments as described in patent EP 1 184 426. These composite pigments may be composed especially of particles comprising a mineral core, at least one binder, which provides for the attachment of the organic pigments to the core, and at least one organic pigment which at least partially covers the core.

The pigment may also be a lake. The term "lake" means dyes adsorbed onto insoluble particles, especially mineral particles, the assembly thus obtained remaining insoluble during use. The mineral substrates onto which the dyes are adsorbed are, for example, alumina, silica, calcium sodium borosilicate, calcium aluminium borosilicate and aluminium. Among the dyes, mention may be made of cochineal carmine. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61

570), D&C Yellow 1 O (CI 77 002), D&C Green 3 (CI 42 053), D&C Blue 1 (CI 42 090). An example of a lake that may be mentioned is the product known under the name D&C Red 7 (CI 15 850:1).

The term "pigments with special effects" means pigments that generally create a coloured appearance (characterized by a certain shade, a certain vivacity and a certain level of luminance) that is non-uniform and that changes as a function of the conditions of observation (light, temperature, angles of observation, etc.). They thus contrast with coloured pigments that afford a standard uniform opaque, semi-transparent or transparent shade.

Several types of pigment with special effects exist: those with a low refractive index, such as fluorescent, photochromic or thermochromic pigments, and those with a high refractive index, such as nacres or glitter flakes.

Examples of pigments with special effects that may be mentioned include nacreous pigments such as titanium mica coated with an iron oxide, mica coated with an iron oxide, mica coated with bismuth oxychloride, titanium mica coated with chromium oxide, titanium mica coated with an organic dye especially of the abovementioned type, and also nacreous pigments based on bismuth oxychloride. They may also be mica particles at the surface of which are superimposed at least two successive layers of metal oxides and/or of organic colorants.

The nacres may more particularly have a yellow, pink, red, bronze, orangey, brown, gold and/or coppery colour or tint. Examples of nacres that may be mentioned include the gold-coloured nacres sold especially by the company Engelhard nder the name Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona), by the company Eckart under the name Prestige Bronze and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nuantique copper 340XB (Cloisonne) and Brown CL4509 (Chromalite); the nacres with a copper tint sold especially by the company Engelhard under the name Copper 340A (Timica) and by the company Eckart under the name Prestige Copper; the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the black nacres with a gold tint sold especially by the company Engelhard under the name Nu antique bronze 240 AB (Timica), the blue nacres sold especially by the company Merck under the name Matte blue (17433) (Microna), Dark Blue (117324) (Colorona), the white nacres with a silvery tint sold especially by the company Merck under the name Xirona Silver, and the golden-green pink-orange nacres sold especially by the company Merck under the name Indian summer (Xirona), and mixtures thereof.

In addition to nacres on a mica support, multilayer pigments based on synthetic substrates such as alumina, silica, sodium calcium borosilicate or calcium aluminium borosilicate, and aluminium, may be envisaged.

Mention may also be made of pigments with an interference effect not bound to a substrate, for instance liquid crystals (Helicones HC from Wacker), holographic interference flakes (Geometric Pigments or Spectra f/x from Spectratek). Special effect pigments also comprise fluorescent pigments, whether these are substances which are fluorescent in daylight or which produce ultraviolet fluorescence, phosphorescent pigments, photochromic pigments, thermochromic pigments and quantum dots, for example sold by Quantum Dots Corporation.

The variety of pigments that may be used in the present invention makes it possible to obtain a wide range of colours, and also particular optical effects such as metallic effects or interference effects.

Preferably, the size of the pigment is generally between 10 nm and 200 µm, preferably between 20 nm and 80 µm and preferentially between 30 nm and 50 µm.

The pigments may be dispersed in the composition by means of a dispersant. The dispersant serves to protect the dispersed particles against agglomeration or flocculation. This dispersing agent can be a surfactant, an oligomer, a polymer or a mixture of several of them carrying one or more functionalities having a strong affinity for the surface of the particles to be dispersed. In particular, they can become physically and/or chemically attached to the surface of the pigments. These dispersants additionally exhibit at least one functional group compatible with or soluble in the continuous medium. In particular, 12-hydroxystearic acid esters and C8 to C20 fatty acid esters of polyols such as glycerol or diglycerol are used, such as poly(12-hydroxystearic acid) stearate with a molecular weight of about 750 g/mol, such as the product sold under the name Solsperse 21 000 by the company Avecia, polyglyceryl-2 dipolyhydroxystearate (CTFA name) sold under the reference Dehymyls PGPH by the company Henkel, or polyhydroxystearic acid such as the product sold under the reference Arlacel P100 by the company Uniqema, and mixtures thereof. Mention may be made, as other dispersant which can be used in the compositions of the invention, of the quaternary ammonium derivatives of polycondensed fatty acids, such as Solsperse 17 000, sold by Avecia, or polydimethylsiloxane/oxypropylene mixtures, such as those sold by Dow Corning under the references DC2-5185 and DC2-5225 C.

The pigments that may be used may be surface-treated with an organic agent. Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described especially in *Cosmetics and Toiletries, February* 1990, vol. 105, pp. 53-64, before being dispersed in the composition in accordance with the invention. These organic agents may be chosen, for example, from amino acids; waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides; polysaccharides, for example chitosan, cellulose and derivatives thereof; polyethylene; (meth)acrylic polymers, for example polymethyl methacrylates; polymers and copolymers containing acrylate units; proteins; alkanolamines; silicone compounds, for example silicones, polydimethylsiloxanes, alkoxysilanes, alkylsilanes and siloxysilicates; organofluorine compounds, for example perfluoroalkyl ethers; fluorosilicone compounds. The surface-treated pigments may also have been treated with a mixture of these compounds and/or may have undergone several surface treatments.

Preferably, the surface-treated pigments are coated with an organic layer. The organic agent with which the pigments are treated can be deposited on the pigments by solvent evaporation, chemical reaction between the molecules of the surface agent or creation of a covalent bond between the surface agent and the pigments.

The surface treatment can thus be carried out, for example, by chemical reaction of a surface agent with the surface of the pigments and creation of a covalent bond between the surface agent and the pigments or fillers. This method is described in particular in U.S. Pat. No. 4,578,266.

Preferably, use will be made of an organic agent covalently bonded to the pigments. The agent for the surface treatment can represent from 0.1% to 50% by weight, preferably from 0.5% to 30% by weight and more preferentially still from 1% to 10% by weight of the total weight of the surface-treated pigments.

Preferably, the surface treatments of the pigments are chosen from the following treatments:
  a PEG-silicone treatment, such as the AQ surface treatment sold by LCW;
  a chitosan treatment, for instance the CTS surface treatment sold by LCW;
  a triethoxycaprylylsilane treatment, for instance the AS surface treatment sold by LCW;
  a methicone treatment, for instance the SI surface treatment sold by LCW;
  a dimethicone treatment, such as the Covasil 3.05 surface treatment sold by LCW;
  a dimethicone/trimethylsiloxysilicate treatment, such as the Covasil 4.05 surface treatment sold by LCW;
  a lauroyllysine treatment, for instance the LL surface treatment sold by LCW;
  a lauroyllysine dimethicone treatment, for instance the LL/SI surface treatment sold by LCW;
  a magnesium myristate treatment, such as the MM surface treatment sold by LCW;
  an aluminium dimyristate treatment, such as the MI surface treatment sold by Miyoshi;
  a perfluoropolymethylisopropyl ether treatment, such as the FHC surface treatment sold by LCW;
  an isostearyl sebacate treatment, such as the HS surface treatment sold by Miyoshi;
  a disodium stearoyl glutamate treatment, for instance the NAI surface treatment sold by Miyoshi;
  a dimethicone/disodium stearoyl glutamate treatment, for instance the SA/NAI surface treatment sold by Miyoshi;
  a perfluoroalkyl phosphate treatment, such as the PF surface treatment sold by Daito;
  an acrylate/dimethicone copolymer and perfluoroalkyl phosphate treatment, such as the FSA surface treatment sold by Daito;
  a polymethylhydrosiloxane/perfluoroalkyl phosphate treatment, such as the FS01 surface treatment sold by Daito;
  a lauroyllysine/aluminium tristearate treatment, for instance the LL-AISt surface treatment sold by Daito;
  an octyltriethylsilane treatment, for instance the OTS surface treatment sold by Daito;
  an octyltriethylsilane/perfluoroalkyl phosphate treatment, for instance the FOTS surface treatment sold by Daito;
  an acrylate/dimethicone copolymer treatment, such as the ASC surface treatment sold by Daito;
  an isopropyl titanium triisostearate treatment, such as the ITT surface treatment sold by Daito;
  a microcrystalline cellulose and carboxymethylcellulose treatment, for instance the AC surface treatment sold by Daito;
  a cellulose treatment, for instance the C2 surface treatment sold by Daito;
  an acrylate copolymer treatment, such as the APD surface treatment sold by Daito;
  a perfluoroalkyl phosphate/isopropyl titanium triisostearate treatment, such as the PF+ITT surface treatment sold by Daito.

Preferably, the composition according to the invention comprises at least one pigment chosen from nacres.

In a particular embodiment of the invention, the cosmetic composition may comprise at least one type of microcapsule.

Microcapsulation processes and the principles on which they are based are described in detail, for example, in *Microencapsulation, Methods and Industrial Application*, published under the direction of Benita, M. Dekker, 1996.

The envelope (or wall) of the microcapsules may comprise at least one water-insoluble polymer and/or a wax.

The term "water-insoluble polymer" means a polymer whose solubility in water at 25° C. is less than 0.1% by weight. The water-insoluble polymer of the envelope may be chosen from:
  polycaprolactone (such as the product sold under the name CAPA640 by the company Solvay), polybutyrolactone, poly(3-hydroxybutyrate);
  poly(C2-C6 alkylene adipates) such as poly(ethylene adipate) or poly(butylene adipate); the term "poly(alkylene adipate)" covers both homopolymers of adipic acid and of an alkanediol and copolymers of linear or branched poly(ester ether) type, obtained from adipic acid and from one or more alkanediols and/or ether diols and/or triols; the alkanediols preferably being straight- or branched-chain C2-C6 alkanediols chosen from ethylene glycol, propylene glycol, 1,3-propanediol, 1,4-butanediol, 1,5-pentanediol, 1,6-hexanediol and neopentyl glycol; the ether diols preferably being di-, tri- or tetra(C2-4 alkylene) glycols such as diethylene glycol, triethylene glycol, tetraethylene glycol, dipropylene glycol, tripropylene glycol, tetrapropylene glycol or dibutylene glycol, tributylene glycol or tetrabutylene glycol. The polyesters of poly(alkylene adipate) type that may be used for the preparation of the microcapsules may also contain a limited number of branching units derived from triols, generally chosen from glycerol, trimethylolethane and trimethylolpropane. Poly(alkylene adipate) polymers are especially described in patent application EP-A-1 029 587.
  polyester polyols of adipic acid and of butanediol, such as the polyester of adipic acid, 1,4-butanediol and 2-ethyl-2-(hydroxymethyl)-1,3-propanediol (such as Lexorez® 1151-35 from the company Inolex). Polyester polyols of adipic acid and of butanediol are especially described in patent application EP-A-1 342 471.
  esters of cellulose and of at least one C1-04 carboxylic acid, such as cellulose acetate, cellulose acetopropionate (for example those sold under the names CAP-482-0.5, CAP-482-20 and CAP-504 by the company Eastman Chemical), cellulose acetobutyrate (for example those sold under the names CAB-551, CAB-500, CAB 553 and CAB-381 by the company Eastman Chemical), and preferably from cellulose acetobutyrate and cellulose acetopropionate;

poly(ortho esters) obtained by polycondensation of polyol, diol lactide and 3,9-diethylidene-2,4,8,10-tetraoxaspiro[5,5]undecane, such as those described in Bouchemal K., Microencapsulation of dehydroepiandrosterone (DHEA) with poly(ortho ester) polymers by interfacial polycondensation, *Journal of Microencapsulation,* 2003, vol. 20, No. 5, 637-651;

poly(ethylene glycol)-poly(butylene terephthalate) block polymers such as those described in the publication Bezemer J. M., Microspheres for protein delivery prepared from amphiphilic multiblock copolymers, *Journal of Controlled Release,* 67 (2000) 233-248;

polyethylene glycol terephthalate/poly (butylene terephthalate) copolymers, such as those described in U.S. Pat. No. 5,980,948;

copolymers of styrene and maleic anhydride, such as those sold under the name SMA by the company Cray Valley;

copolymers of styrene and acrylic acid, such as the product sold under the name Plioway Ultra 200 by the company Plioway;

styrene-ethylene/butylene-styrene or styrene-ethylene/propylene-styrene block terpolymers, such as those sold under the name Kraton G by the company Shell;

terpolymers of ethylene, vinyl acetate and maleic anhydride, such as those sold under the name Arevac by the company Arkema;

and mixtures thereof.

The wax of the envelope may be chosen from beeswax, polyglycerolated beeswax, hydrogenated plant oils, paraffin with a melting point above 45° C., and silicone waxes. Examples of silicone waxes that may be mentioned include alkyl or alkoxy dimethicones comprising from 16 to 45 carbon atoms, for instance behenoxy dimethicone and C16-C45 dimethiconol alkyl esters such as dimethiconol behenate. For the purposes of the present invention, a wax is a lipophilic compound, which is solid at room temperature (about 25° C.), with a reversible solid/liquid change of state, having a melting point greater than about 40° C., which may be up to 200° C., and having in the solid state anisotropic crystal organization. Preferably, the core of the microcapsules is aqueous.

Preferably, the composition according to the invention comprises the pigment(s) and/or the microcapsule(s) in a total amount of from 0.01% to 40% by weight, preferably from 0.05% to 30% by weight, or even from 0.1% to 20% by weight, better still from 0.5% to 15% by weight, or even from 1% to 10% by weight, relative to the total weight of the composition.

Other Ingredients

The compositions according to the invention may also comprise one or more surfactants chosen especially from anionic, amphoteric, cationic and nonionic surfactants. Preferably, the compositions comprise at least one nonionic surfactant.

The nonionic surfactants that may be present in the composition according to the invention are especially described in the *Handbook of Surfactants* by M. R. Porter, published by Blackie & Son (Glasgow and London), 1991, pp. 116-178. Mention may be made of the following nonionic surfactants:

oxyalkylenated (C8-C24)alkylphenols;

saturated or unsaturated, linear or branched, oxyalkylenated or glycerolated C8-C40 alcohols, comprising one or two fatty chains;

saturated or unsaturated, linear or branched, oxyalkylenated C8-C30 fatty acid amides;

esters of saturated or unsaturated, linear or branched, C8-C30 acids and of polyethylene glycols;

preferably oxyethylenated esters of saturated or unsaturated, linear or branched, C8-C30 acids and of sorbitol;

fatty acid esters of sucrose or of pentaerythritol;

(C8-C30)alkyl(poly)glycosides and (C8-C30)alkenyl (poly)glycosides, which are optionally oxyalkylenated (1 to 10 oxyalkylene units) and comprising from 1 to 15 glucose units, (C8-C30)alkyl(poly)glucoside esters;

saturated or unsaturated, oxyethylenated plant oils;

condensates of ethylene oxide and/or of propylene oxide, alone or as mixtures;

N—(C8-C30)alkylglucamine and N—(C8-C30)acylmethylglucamine derivatives;

aldobionamides;

amine oxides;

oxyethylenated and/or oxypropylenated silicones;

and mixtures thereof.

The oxyalkylene units are more particularly oxyethylene or oxypropylene units, or a combination thereof, preferably oxyethylene units. The number of moles of ethylene oxide and/or propylene oxide preferably ranges from 1 to 250, more particularly from 2 to 100 and better still from 2 to 50; the number of moles of glycerol ranges especially from 1 to 50 and better still from 1 to 10. Advantageously, the nonionic surfactants do not comprise any oxypropylene units.

As examples of glycerolated nonionic surfactants, mention may be made of monoglycerolated or polyglycerolated C8-C40 alcohols, comprising from 1 to 50 mol of glycerol and preferably from 1 to 10 mol of glycerol. Mention may thus be made of lauryl alcohol containing 4 mol of glycerol (INCI name: polyglyceryl-4 lauryl ether), lauryl alcohol containing 1.5 mol of glycerol, oleyl alcohol containing 4 mol of glycerol (polyglyceryl-4 oleyl ether), oleyl alcohol containing 2 mol of glycerol (polyglyceryl-2 oleyl ether), cetearyl alcohol comprising 2 mol of glycerol, cetearyl alcohol comprising 6 mol of glycerol, oleocetyl alcohol comprising 6 mol of glycerol, and octadecanol comprising 6 mol of glycerol. Among the glycerolated alcohols, it is more particularly preferred to use a C8/C10 alcohol containing 1 mol of glycerol, a C10/C12 alcohol containing 1 mol of glycerol and a C12 alcohol containing 1.5 mol of glycerol.

The nonionic surfactants are preferentially chosen from:

oxyethylenated C8-C40 alcohols comprising from 1 to 100 mol of ethylene oxide, preferably from 2 to 50 and more particularly from 2 to 40 mol of ethylene oxide and comprising one or two fatty chains;

saturated or unsaturated oxyethylenated plant oils comprising from 1 to 100 and preferably from 2 to 50 mol of ethylene oxide;

(C8-C30)alkyl(poly)glycosides, which are optionally oxyalkylenated (1 to 10 OE) and comprising 1 to 15 glucose units;

monoglycerolated or polyglycerolated C8-C40 alcohols, comprising from 1 to 50 mol of glycerol and preferably from 1 to 10 mol of glycerol;

saturated or unsaturated, linear or branched, oxyalkylenated C8-C30 fatty acid amides;

esters of saturated or unsaturated, linear or branched, C8-C30 acids and of polyethylene glycols, sucrose or pentaerythritol;

and mixtures thereof.

Preferentially, the nonionic surfactants are chosen from:

saturated or unsaturated, linear or branched, oxyalkylenated C8-C40 alcohols, comprising one or two fatty chains, especially ceteareth-60 myristyl glycol;

(C8-C30)alkyl(poly)glycosides, especially caprylyl/capryl glucoside;

esters of saturated or unsaturated, linear or branched, C8-C30 acids and of polyethylene glycols, sucrose or pentaerythritol and especially pentaerythrityl tetraisostearate;

and mixtures thereof.

The composition according to the invention may also comprise at least one or more common cosmetic ingredients chosen especially from propellants; sunscreens; protein hydrolysates; moisturizers; antidandruff agents; antioxidants; chelating agents; reducing agents; oxidation bases, couplers, oxidizing agents, direct dyes; relaxants; hydroxy acids; silicones, in particular polydimethylsiloxanes (PDMSs); fragrances; conditioning polymers; basifying or acidifying agents; silanes. A person skilled in the art will take care to choose the ingredients included in the composition, and also the amounts thereof, such that they do not harm the properties of the compositions of the present invention.

The composition according to the invention may be aqueous or anhydrous. It is advantageously anhydrous.

For the purposes of the present invention, the term "anhydrous" refers to a composition comprising less than 5% by weight of water, preferably less than 2% by weight of water and better still less than 1% by weight of water; preferentially, the composition does not comprise any added water (0%), any water that may be present being water originating from the hygroscopic starting materials or water of crystallization of the salts.

The compositions according to the invention may be in any galenical form conventionally used and especially in the form of an alcoholic or oily solution or suspension; a solution or dispersion of the lotion or serum type; a gel, especially an anhydrous gel, or of any other cosmetic form.

The cosmetic composition according to the invention especially finds a particularly advantageous application in the hair sector, especially for caring for and/or conditioning the hair.

The hair compositions are preferably hair conditioners, styling or care gels, care lotions, blow-drying lotions, conditioners, masks, sera, fixing and styling compositions; and are preferentially in the form of hair oils or sera.

Preferably, the composition according to the invention has a viscosity, measured at 25° C. and 1 atm, of between 100 cp and 20 000 cp (centipoises), i.e. between 100 mPa·s and 20 Pa·s.

The cosmetic composition, especially a hair composition, may or may not be rinsed out after having been applied to the keratin materials, especially the hair. It is thus optionally possible to perform rinsing, for example with water, after an optional leave-in time.

Advantageously, the composition according to the invention is a hair composition, which is preferably not rinsed out, and is especially intended for curly or frizzy hair, in particular sensitized hair.

As indicated above, a subject of the invention is also a cosmetic treatment process, especially for caring for, cleansing and/or conditioning keratin materials, especially the hair, in particular curly or frizzy hair, comprising the application to the said materials of a cosmetic composition according to the invention.

A subject of the invention is also a cosmetic process for treating the hair, especially for caring for, cleansing and/or conditioning the hair, comprising the application of a cosmetic composition comprising:

(a) one or more liquid fatty esters in an amount ranging from 10% to 40% by weight relative to the total weight of the composition, (b) one or more volatile oils, other than the liquid fatty esters (a), in an amount of greater than or equal to 30% by weight relative to the total weight of the composition, and (c) one or more thickeners chosen from optionally hydrogenated block, especially diblock or triblock, copolymers of styrene and of olefin, preferably containing one or two ethylenic unsaturations, and/or preferably containing from 2 to 5 carbon atoms.

It is optionally possible to perform rinsing, for example with water, after an optional leave-in time.

The processes are in particular hair treatment processes for caring for and/or conditioning the hair, in particular curly or frizzy hair, in particular sensitized hair.

The present invention is illustrated in greater detail in the examples that follow (AM=active material).

EXAMPLE 1

A hair composition of leave-in hair-conditioning type, for caring for and conditioning the hair, is prepared, comprising:

| Ingredient | % by weight |
| --- | --- |
| Isopropyl myristate | 10% |
| Styrene/ethylene-propylene diblock copolymer (Kraton ® G1701) | 4% |
| Isononyl isononanoate | 5% |
| Pentaerythrityl tetraisostearate | 5% |
| Fragrance | qs |
| Isododecane | qs 100% |

An anhydrous haircare composition is obtained.

The said composition is applied to the hair; it makes it possible to reduce the frizziness, while at the same time giving the hair sheen and a pleasant feel.

EXAMPLE 2

A hair composition of leave-in hair-conditioning type, for caring for and conditioning the hair, is prepared, comprising:

| Ingredient | % by weight |
| --- | --- |
| Premix comprising 27.6% of styrene/ethylene-propylene diblock copolymer (Kraton ® G1701) + 72.4% of isopropyl myristate | 15% (i.e. 4.1% of polymer AM) |
| Pentaerythrityl tetraisostearate | 10% |
| Fragrance | qs |
| Isododecane | qs 100% |

An anhydrous haircare composition is obtained.

The said composition is applied to the hair; it makes it possible to reduce the frizziness, while at the same time giving the hair sheen and a pleasant feel.

EXAMPLE 3

A hair composition of leave-in hair-conditioning type, for caring for and conditioning the hair, is prepared, comprising:

| Ingredient | % by weight |
|---|---|
| Premix comprising 16% of styrene/ethylene-propylene diblock copolymer (Kraton ® G1701) + 84% of isopropyl myristate | 30% (i.e. 4.8% of polymer AM) |
| Capric/caprylic acid triglycerides (Miglyol 812 N) | 10% |
| Fragrance | qs |
| Isododecane | qs 100% |

An anhydrous haircare composition is obtained.

The said composition is applied to the hair; it makes it possible to reduce the frizziness, while at the same time giving the hair sheen and a pleasant feel.

EXAMPLE 4

A hair composition of leave-in hair-conditioning type, for caring for and conditioning the hair, is prepared, comprising:

| Ingredient | % by weight |
|---|---|
| Premix comprising 16% of styrene/ethylene-propylene diblock copolymer (Kraton ® G1701) + 84% of isopropyl myristate | 30% (i.e. 4.8% of polymer AM) |
| Isohexadecane | 10% |
| Fragrance | qs |
| Isododecane | qs 100% |

An anhydrous haircare composition is obtained.

The said composition is applied to the hair; it makes it possible to reduce the frizziness, while at the same time giving the hair sheen and a pleasant feel.

EXAMPLE 5

A hair composition of leave-in hair-conditioning type, for caring for and conditioning the hair, is prepared, comprising:

| Ingredient | % by weight |
|---|---|
| Isopropyl myristate | 10% |
| Styrene/ethylene-propylene diblock copolymer (Kraton ® G1701) | 4% |
| Isononyl isononanoate | 5% |
| Pentaerythrityl tetraisostearate | 5% |
| Calcium aluminium borosilicate platelets coated with titanium oxide and tin oxide, treated with silica (Ronastar Noble Sparks SQ from Merck) | 0.1% |
| Green dye (Green 6) | qs |
| Fragrance | qs |
| Isododecane | qs 100% |

A coloured anhydrous haircare composition with nacreous tints is obtained.

The said composition is applied to the hair; it makes it possible to reduce the frizziness, while at the same time giving the hair sheen and a pleasant feel.

EXAMPLE 6

A gelled hair composition of leave-in hair-conditioning type, for caring for and conditioning the hair, is prepared, comprising:

| Ingredient | % by weight |
|---|---|
| Isopropyl myristate | 10.9% |
| Styrene/ethylene-propylene diblock copolymer (Kraton ® G1701) | 10.7% |
| Isononyl isononanoate | 5% |
| Pentaerythrityl tetraisostearate | 5% |
| Calcium sodium borosilicate (and) titanium dioxide (and) silica (and) iron oxides (and) tin oxide (Ronastar Golden Jewel SQ from Merck) | 0.35% |
| Mica/titanium oxide/iron oxide (Colorona Red Gold from Merck) | 2.35% |
| Fragrance | qs |
| Isododecane | qs 100% |

A gelled anhydrous composition with nacreous tints, for caring for and conditioning the hair, is obtained.

The said composition is applied to the hair; it makes it possible to reduce the frizziness, while at the same time giving the hair sheen and a pleasant feel.

The invention claimed is:
1. A cosmetic composition comprising:
 (a) at least one liquid fatty ester, present in an amount ranging from 10% to 40% by weight, relative to the total weight of the composition,
 (b) at least one volatile oil chosen from branched $C_8$-$C_{16}$ alkanes, present in an amount greater than or equal to about 30% by weight, relative to the total weight of the composition,
 (c) at least one thickener, and
 (d) at least one insoluble particle,
 wherein the at least one liquid fatty ester and the at least one thickener are present in a weight ratio ranging from 1 to about 5.
2. The cosmetic composition according to claim 1, wherein the at least one liquid fatty ester is chosen from:
 esters of monoalcohols or of polyols with monocarboxylic or polycarboxylic acids, wherein at least one of the alcohols and/or acids comprise at least one hydrocarbon-based chain containing at least 6 carbon atoms;
 esters of a fatty acid containing at least 6 carbon atoms and of a monoalcohol; or
 esters of a fatty monoacid containing at least 6 carbon atoms and of a monoalcohol.
3. The cosmetic composition according to claim 1, wherein the at least one liquid fatty ester is chosen from compounds corresponding to formula

R1-COOR2, wherein:

R1 is chosen from a linear or branched, saturated or unsaturated, optionally mono- or polyhydroxylated hydrocarbon-based radical, containing from 5 to 31 carbon atoms; or a linear or branched alkyl radical containing from 7 to 21 carbon atoms; and
 R2 is chosen from a linear or branched, saturated or unsaturated, optionally mono- or polyhydroxylated hydrocarbon-based radical, containing from 1 to 20 carbon atoms; a linear alkyl radical containing from 1 to 4 carbon atoms; a branched alkyl radical containing from 3 to 20 carbon atoms or from 3 to 16 carbon atoms; or a branched saturated alkyl radical containing from 3 to 12 carbon atoms.
4. The cosmetic composition according to claim 1, wherein the at least one liquid fatty ester is chosen from isopropyl myristate, ethyl myristate, butyl myristate, isobutyl myristate, 2-octyldodecyl myristate, 2-ethylhexyl monococoate, ethyl palmitate, isopropyl palmitate, isobutyl palmitate, 2-ethylhexyl palmitate, butyl stearate, isopropyl stearate, isobutyl stearate, isocetyl stearate, isostearyl isostearate, isopropyl isostearate, 2-ethylhexyl stearate, isononyl isononanoate, 2-ethylhexyl hydroxystearate, decyl oleate, or mixtures thereof.

5. The cosmetic composition according to claim 1, wherein the liquid fatty ester is present in an amount ranging from 10% to 35% by weight, relative to the total weight of the composition.

6. The cosmetic composition according to claim 1, wherein the at least one volatile oil is chosen from isododecane, isodecane, isohexadecane, or mixtures thereof.

7. The cosmetic composition according to claim 1, wherein the at least one volatile oil is present in an amount ranging from 30% to 98% by weight, relative to the total weight of the composition.

8. The cosmetic composition according to claim 1, wherein the at least one thickener is chosen from block, diblock, triblock, multiblock, radial or star polymers, optionally hydrogenated block, diblock or triblock polymers; or copolymers of styrene and olefin containing one or two ethylenic unsaturations and/or from 2 to 5 carbon atoms.

9. The cosmetic composition according to claim 1, wherein the at least one thickener is chosen from:
- optionally hydrogenated diblock copolymers bearing styrene blocks and ethylene/C3-C4 alkylene blocks or bearing styrene blocks and ethylene/propylene or ethylene/butylene blocks;
- optionally hydrogenated diblock copolymers, bearing styrene and ethylene/butadiene blocks;
- optionally hydrogenated triblock copolymers of styrene-ethylene/propylene-styrene, styrene-ethylene/butadiene-styrene, styrene-isoprene-styrene or styrene-butadiene-styrene; or
- a mixture of styrene-butylene/ethylene-styrene triblock hydrogenated copolymers and of ethylene-propylene-styrene hydrogenated star polymers.

10. The cosmetic composition according to claim 1, wherein the thickener is present in an amount ranging from 0.1% to 20% by weight, relative to the total weight of the composition.

11. The cosmetic composition according to claim 1, wherein the at least one insoluble particle is chosen from pigments, microcapsules, or mixtures thereof; mineral pigments, organic pigments, lakes, pigments with special effects, nacres, glitter flakes, or microcapsules whose envelope comprises at least one water-insoluble polymer and/or a wax.

12. The cosmetic composition according to claim 1, wherein the insoluble particle in present in a total amount ranging from 0.01% to 40% by weight, relative to the total weight of the composition.

13. The cosmetic composition according to claim 1, wherein the composition is anhydrous.

14. The cosmetic composition according to claim 1, having a viscosity, measured at 25° C. and 1 atm, ranging from 100 cP to 20 000 cP.

15. The cosmetic composition according to claim 1, further comprising at least one surfactant chosen from anionic, amphoteric, cationic, or nonionic surfactants.

16. The cosmetic composition according to claim 15, wherein the at least one surfactant is chosen from nonionic surfactants.

17. The cosmetic composition according to claim 1, further comprising at least one cosmetic ingredient chosen from propellants, sunscreens, protein hydrolysates, moisturizers, antidandruff agents, antioxidants, chelating agents, reducing agents, oxidation bases, couplers, oxidizing agents, direct dyes, relaxants, hydroxy acids, silicones, PDMSs, fragrances, conditioning polymers, basifying agents, acidifying agents, silanes, or mixtures thereof.

18. A cosmetic process for treating keratin materials, comprising:
applying to said keratin materials a cosmetic composition comprising:
  (a) at least one liquid fatty ester, present in an amount ranging from 10% to 40% by weight, relative to the total weight of the composition,
  (b) at least one volatile oil chosen from branched $C_8$-$C_{16}$ alkanes other than the at least one liquid fatty ester (a), present in an amount greater than or equal to about 30% by weight, relative to the total weight of the composition,
  (c) at least one thickener, and
  (d) at least one insoluble particle,
  wherein the at least one liquid fatty ester and the at least one thickener are present in a weight ratio ranging from 1 to 5; and
optionally rinsing the keratin materials.

19. A cosmetic process for treating the hair comprising:
applying to said hair a cosmetic composition comprising:
  (a) at least one liquid fatty ester, present in an amount ranging from 10% to 40% by weight, relative to the total weight of the composition,
  (b) at least one volatile oil, other than the liquid fatty esters (a), present in an amount greater than or equal to about 30% by weight, relative to the total weight of the composition, and
  (c) at least thickener chosen from optionally hydrogenated block, diblock, or triblock copolymers of styrene and of olefin, containing one or two ethylenic unsaturations, or from 2 to 5 carbon atoms,
  (d) optionally at least one insoluble particle, chosen from pigments, nacres or microcapsules; and
optionally rinsing the hair.

* * * * *